US006826336B2

United States Patent
Guy

(10) Patent No.: US 6,826,336 B2
(45) Date of Patent: Nov. 30, 2004

(54) FIBER OPTIC LED ILLUMINATOR

(75) Inventor: James K. Guy, Mesa, AZ (US)

(73) Assignee: The Boeing Company, Chicago, IL (US)

( * ) Notice: Subject to any disclaimer, the term of this patent is extended or adjusted under 35 U.S.C. 154(b) by 195 days.

(21) Appl. No.: 10/154,608

(22) Filed: May 22, 2002

(65) Prior Publication Data

US 2003/0219207 A1 Nov. 27, 2003

(51) Int. Cl.$^7$ ................................................ G02B 6/30
(52) U.S. Cl. ............................ 385/49; 385/88; 385/93; 385/94
(58) Field of Search ............................. 385/88–94, 49

(56) References Cited

U.S. PATENT DOCUMENTS

| | | | | | |
|---|---|---|---|---|---|
| 4,182,545 A | * | 1/1980 | Greer | ........................ | 385/88 |
| 4,257,672 A | * | 3/1981 | Balliet | ........................ | 385/35 |
| 4,279,465 A | * | 7/1981 | Vojvodich | ................... | 385/88 |
| 4,433,898 A | * | 2/1984 | Nasiri | ........................ | 385/91 |
| 4,439,006 A | * | 3/1984 | Stevenson | .................... | 385/88 |
| 4,599,537 A | * | 7/1986 | Yamashita | ................. | 313/501 |
| 4,818,056 A | * | 4/1989 | Enochs et al. | ................ | 385/88 |
| 5,175,783 A | * | 12/1992 | Tatoh | ........................ | 385/93 |
| 5,467,419 A | * | 11/1995 | Roff et al. | ..................... | 385/92 |
| 5,485,317 A | * | 1/1996 | Perissinotto et al. | ........ | 359/712 |
| 5,495,545 A | * | 2/1996 | Cina et al. | ..................... | 385/92 |
| 5,504,828 A | * | 4/1996 | Cina et al. | ..................... | 385/33 |
| 5,604,361 A | * | 2/1997 | Isaksson | ...................... | 257/99 |
| 5,692,083 A | * | 11/1997 | Bennett | ....................... | 385/88 |
| 5,815,623 A | * | 9/1998 | Gilliland et al. | .............. | 385/93 |
| 5,993,075 A | * | 11/1999 | Huang et al. | ................. | 385/92 |
| 6,264,376 B1 | * | 7/2001 | Savage, Jr. | ................... | 385/88 |
| 6,411,323 B1 | * | 6/2002 | Waarts et al. | ............... | 347/241 |
| 6,572,280 B2 | * | 6/2003 | Hurt et al. | ..................... | 385/92 |

* cited by examiner

*Primary Examiner*—Ellen E. Kim
(74) *Attorney, Agent, or Firm*—Shimokaji & Associates, P.C.

(57) ABSTRACT

A fiber fed illumination system includes a solid-state light source, such as an LED; a light guide, such as a fiber optic; and a coupling assembly. The light emitting surface of the light source may be flat or concave. In the coupling assembly the light guide is placed either next to the flat surface or at the aperture of the concave surface. The light guide may be bonded directly to the light source or bonded so that index matching optical gel resides between the light emitting surface and the light guide. The coupling assembly includes a cavity surrounding the light emitting surface with a feature for retaining the light guide in proximity to the light source. The cavity is filled with index matching optical gel. The size of the light guide matches the size of the solid-state light source in order to provide the smallest feasible light guide.

22 Claims, 2 Drawing Sheets

FIBER OPTIC LED ILLUMINATOR

BACKGROUND OF THE INVENTION

The present invention generally relates to fiber optic illumination systems and, more particularly, to fiber optic illumination systems using a solid-state illumination device such as a light emitting diode.

Fiber optic illumination systems are designed to meet specific requirements that a standard illumination system cannot meet, for example, Illumination into volatile areas, into the human body, and into remote sites. Fiber optic illumination systems generally include a light source, a light guide device for transmitting the light from the light source to where it is needed, and an optical coupling of the light source to the light guide. Electric arc light is typically used as a high intensity light source. The light guide may be, for example, a fiber optic, fiber bundle, or wave-guide device.

The typical current method for optically coupling a light guide to the source is to provide a reflector or optic to focus the source light onto the target area of the light guide so that an illuminated area includes a spot of light falling on the face of the light guide. The spot size at the face of the light guide is a geometric function of the size of the source, i.e., there is positive magnification of the source light so that the spot size cannot be smaller than the size of the original light source. The geometric function depends on the angle of incidence of the cone of light that is impinging on the face of the light guide in such a way that, if the angle of incidence increases, the area illuminated decreases. In practice, for example, the spot size produced by an elliptical reflector is determined according to a geometrical equation, but leads to a spot size approximately four times bigger than the original light source. Such magnification requires a big light guide to couple all the source light energy, and the intensity of the light is spread over the larger spot area, lowering the light intensity per unit area.

One commonly used criterion for determining the light gathering power of an optical system is the concept of "etendue". Etendue may be used to determine absolute values for the emitted (reflected or transmitted) energy, in order to control the overall energy balance in the optical system. Etendue may be defined as the product of radiant flux density and the area of a radiating or receiving surface. This product is a constant. So, if the angle of the incident cone increases, the area illuminated decreases. For a fiber optic, the highest angle of light that is accepted into the core of the fiber defines the numerical aperture (NA). For example, the numerical aperture can be determined by the differences in the indices of refraction of the core and cladding of the optical fiber and can be calculated using Snell's law. An alternative way to calculate etendue for a fiber bundle is by multiplying the core area by the acceptance angle, i.e., the numerical aperture. The object of providing an efficient coupling is to capture all of the light rays. By matching the etendue of the light source to the etendue of the optical fiber, more of the light rays enter the fiber and stay in via total internal reflection (TIR). No system of external optics can increase the etendue of an optical system. This principle is called conservation of etendue. Thus, the most efficient optical coupling matches the etendue of the source to the etendue of the receiving light guide.

The current trend toward high intensity light emitting diode (LED) illumination has led to the ability to produce LEDs with efficacies near that of high intensity arc light sources. There has, therefore, arisen a need for the ability to couple a solid-state illumination device, such as an LED, to a fiber optic to support the features desired by fiber fed illumination systems. There has also arisen a need for the ability to provide the levels of intensity equal to that of other light sources. There are specific benefits in the use of narrow band illuminators, for example, ultra-violet (UV), blue, green, red, and near infrared (NIR). These narrow bands have been achieved through filtering of a standard white light source, which yielded low system efficiency as most of the light was thrown away as waste heat. The narrow band LED light sources, if efficiently coupled to fiber fed illumination systems, can give specific discrete bands required for special applications such as aircraft position and formation lighting or medical endoscopy.

As can be seen, there is a need for coupling a solid-state illumination device to a fiber optic to support the features desired by fiber fed illumination systems. Also, there is a need for coupling a solid-state illumination device to a fiber fed illumination system, which maximizes the coupling into the smallest feasible light guide. Moreover, there is a need for efficient coupling of narrow band LED light sources to fiber fed illumination systems.

SUMMARY OF THE INVENTION

The present invention provides coupling of a solid-state illumination device to a fiber optic to support the features desired by fiber fed illumination systems. The present invention also provides coupling of a solid-state illumination device to a fiber fed illumination system, which maximizes the coupling into the smallest feasible light guide. Moreover, the present invention provides efficient coupling of narrow band LED light sources to fiber fed illumination systems.

In one aspect of the present invention, a fiber fed illumination system includes a solid-state light source, which has a light emitting surface, a light guide, and a coupling assembly. In the coupling assembly the light guide is placed next to the light emitting surface of the solid-state light source, so that light from the solid-state light source is transmitted within the light guide.

In another aspect of the present invention, a fiber fed illumination system includes a solid-state light source having a light emitting surface, a light guide, and a coupling assembly. In the coupling assembly the light guide is placed next to the light emitting surface of the solid-state light source and the light guide is bonded to the light source. The coupling assembly further includes a plastic dome with a hole having the proper dimensions to accept the light guide. The plastic dome forms a cavity surrounding the light emitting surface, and the cavity is filled with an optical gel. Light from the solid-state light source is transmitted within the light guide.

In still another aspect of the present invention, a coupling assembly for optically coupling a light guide to a solid-state light source having a light emitting surface includes a plastic dome with a hole. The hole has proper dimensions to accept the light guide, and the plastic dome forms a cavity surrounding the light emitting surface. The cavity is filled with an optical gel, and the light guide is adjacent to the light emitting surface so that light from the solid-state light source is transmitted within the light guide.

In yet another aspect of the present invention, a fiber fed illumination system includes an LED light source having a light emitting surface; a light guide comprising a fiber optic; and a coupling assembly. In the coupling assembly, the light guide is placed next to the light emitting surface of the solid-state light source and the light guide is bonded to the light source. The coupling assembly further includes a plastic dome with a hole having the proper dimensions to accept the light guide. The plastic dome forms a cavity surrounding the light emitting surface and the cavity is filled with an optical gel. The size of the solid-state light source substantially matches the size of the light guide, and light from the solid-state light source is transmitted within the light guide.

In a further aspect of the present invention, a method of optically coupling a light guide to a solid-state light source includes steps of: providing a solid-state light source having a light emitting surface; substantially matching a size of the light guide to a size of the solid-state light source, whereby a smallest feasible light guide is used; placing the light guide next to the light emitting surface; and transmitting light from the solid-state light source through the light guide. The solid-state light source may have a concave shaped light emitting surface to provide maximized coupling by placing the light guide at the aperture of the concave shaped light emitting surface.

These and other features, aspects and advantages of the present invention will become better understood with reference to the following drawings, description and claims.

DETAILED DESCRIPTION OF THE INVENTION

Figure 1:
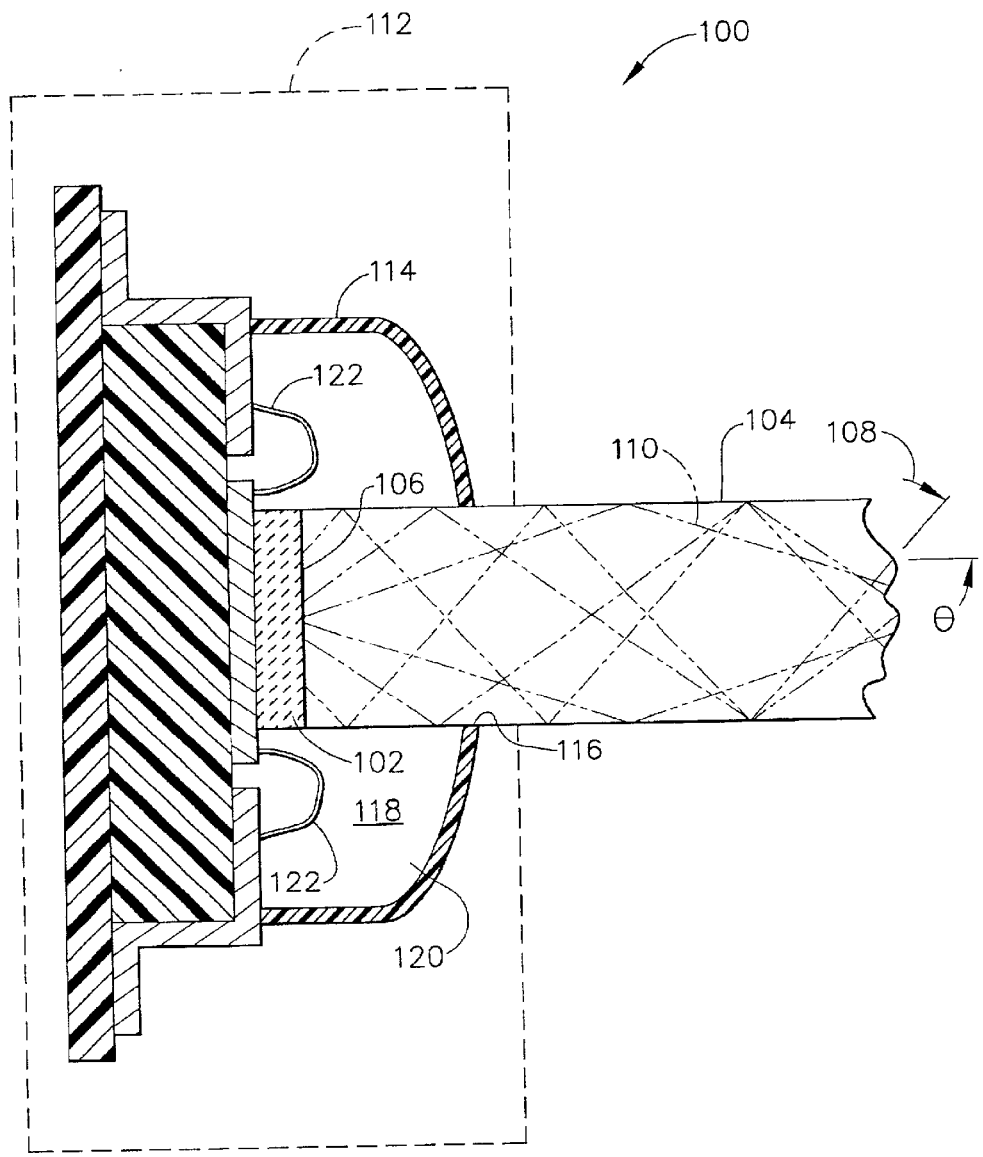
FIG. 1 is a cross sectional diagram of a solid-state light source optically coupled to a light guide according to one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention provides coupling of a solid-state illumination device to a fiber optic for use in fiber fed illumination systems. Such systems may be used, for example, for Illumination into volatile areas, into the human body, and into remote sites. Fiber fed illumination systems coupled to narrow band light emitting diode (LED) light sources in accordance with one embodiment can provide illumination in specific discrete bands required for special applications such as aircraft position and formation lighting or medical endoscopy.

In one embodiment, the present invention provides optical coupling of a solid-state illumination device to the light guide in a fiber fed illumination system. The solid-state illumination device may be an LED light source and the light guide may be a fiber optic, fiber bundle, i.e., multiple fiber optics bundled together, or a wave-guide device, for example. In one embodiment, the present invention shows how to most effectively couple the light guide to the LED source. The current prior art methods for coupling a light guide to a light source typically include providing a reflector or optic to focus the source light onto the target area of the light guide so that an illuminated area includes a spot of light falling on the face of the light guide. The spot size at the face of the light guide cannot, in this application to a fiber fed illumination system, be smaller than the size of the light source, i.e., there is positive magnification so that the spot is always bigger than the source. In general, the spot size falling on the face of the light guide may typically be four times larger than the size of the light source, thus, requiring a large light guide to couple the maximum amount of light, and spreading the light over the large spot area, lowering the intensity per unit area of the light. In contrast to the prior art, the optical coupling of the present invention maximizes the coupling of light from the source into the smallest feasible light guide.

Conventional red LEDs generally have a truncated inverted pyramid (TIP) structure or cubic structure. Typically, the red LEDs have a lead, i.e., electrical connection, in the center of the top of the device and the emitting surface is on the side or sides so that light is emitted from the sides of either the cubic or truncated inverted pyramid structure of the LED and not the top. High intensity LEDs in the blue through green spectrum are different from the conventional red LED configuration. The high intensity blue through green spectrum LEDs are top surface emitters. The electrical leads are bonded near the sides of the device on the green and blue LEDs, leaving a clear path to bring a light guide into close proximity of the LED's light emitting surface.

By placing the optical fiber or fiber bundle next to the surface emitting die of the LED, one embodiment reduces the size of the spot. By reducing the spot size falling on the face of the light guide, the embodiment maximizes the coupling of light from the source LED into the smallest feasible light guide.

Referring now to FIG. 1, fiber fed illumination system 100 is illustrated according to one embodiment. Fiber fed illumination system 100 includes solid-state light source 102. For example, solid-state light source 102 may be an LED. Fiber fed illumination system 100 also includes light guide 104. For example, light guide 104 may be a fiber optic, a fiber bundle, or a wave-guide. Solid-state light source 102 has a light emitting surface 106. Light guide 104 may be placed in intimate contact with the light emitting surface 106 so that light emitted from light emitting surface 106 of solid-state light source 102 which is within the numerical aperture of the light guide may be captured by light guide 104 and is transmitted within light guide 104 by total internal reflection (TIR). For example, light guide 104 may be bonded to light emitting surface 106 of solid-state light source 102.

The size of light emitting surface 106 of solid-state light source 102 and the size of light guide 104 may be chosen so that the etendue of solid-state light source 102 closely approximates, or matches, the etendue of light guide 104. Thus, the angle of incidence 108, labeled "θ" in FIG. 1, may be within the numerical aperture (NA) of light guide 104 for most of the light rays 110 emitted by solid-state light source 102. By maximizing the amount of light rays 110 captured, the smallest feasible size may be used for light guide 104. For example, in one embodiment, a 1-millimeter (mm) square LED die was matched to a fiber bundle of seven hex packed 0.5 mm fibers. The length from tip to tip of the square die equals 1.414 mm, which closely approximates the diameter of the fiber bundle, which is 1.36 mm. The fiber bundle can be heat swaged to reduce the interstitial losses and form a desired shape (pseudo-square). Alternatively, the LED die can be cut to a shape that matches the light guide or fiber bundle. The fiber bundle may also be hard epoxied into place against the LED and then strain relieved using a flexible epoxy to stabilize the assembly.

Fiber fed illumination system 100 may also include coupling assembly 112. Coupling assembly 112 may include plastic dome 114. Plastic dome 114 may be drilled to form a hole 116 of proper dimensions to accept light guide 104. Coupling assembly 112 may include a cavity 118, surrounding light emitting surface 106 of solid-state light source 102. Cavity 118 may be filled with optical gel 120, which may be an index matching gel for the purpose of bridging the gap, i.e., transmitting light, between the light source and the light guide when the light guide is not bonded to the light emitting surface. Fiber fed illumination system 100 may also include lead wires 122 for providing electrical connection to a source of power for solid-state light source 102.

Figure 2:
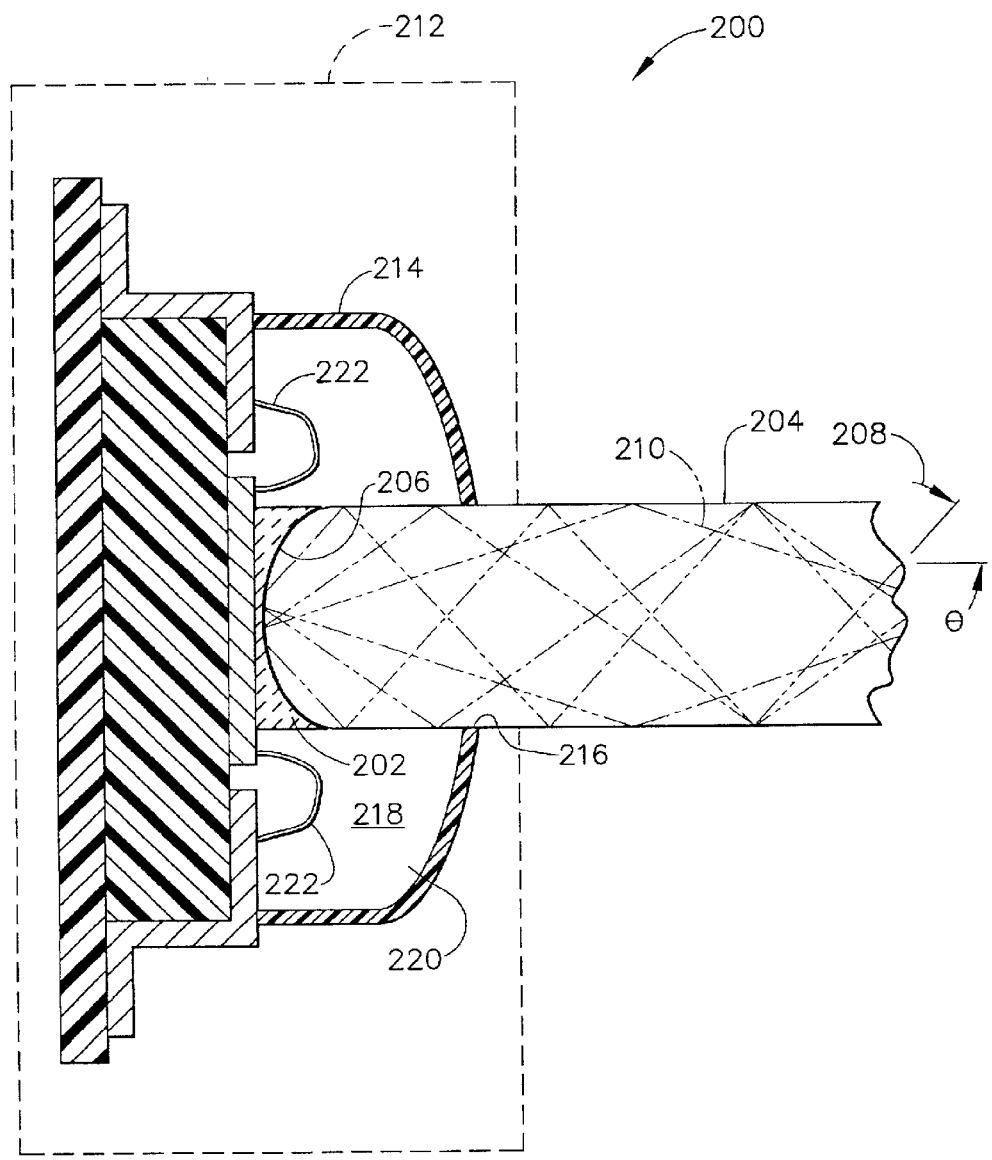
FIG. 2 is a cross sectional diagram of a solid-state light source with a concave light emitting surface optically coupled to a light guide according to one embodiment of the present invention.

Referring now to FIG. 2, fiber fed illumination system 200 is illustrated according to one embodiment. Fiber fed illumination system 200 includes solid-state light source 202. For example, solid-state light source 202 may be an LED. Fiber fed illumination system 200 also includes light guide 204. For example, light guide 204 may be a fiber optic, a fiber bundle, or a wave-guide. Solid-state light source 202 may have a concave light emitting surface 106. For example, concave light emitting surface 106 may be spherical, or may be a paraboloid of revolution or an ellipsoid of revolution. Other concave shapes may be used depending on the particular solid-state light source 202 or the aperture through which light is to be emitted by solid-state light source 202, the particular light guide 204 being used, and the specific application of fiber fed illumination system 200, for example.

Light guide 204 may be placed at the aperture of the concave light emitting surface 206 so that light emitted from concave light emitting surface 206 of solid-state light source 202 is coupled efficiently into the light guide 204 and remains within the light guide 204 by total internal reflection (TIR). For example, light guide 204 may be bonded to concave light emitting surface 206 of solid-state light source 202 if the shape of the light guide's first surface matches the contour of the light emitting surface. Alternatively, optical coupling may be improved by using index matching optical gel to fill in any gap between the light guide and light emitting surface due to differences in contour.

The size of concave light emitting surface 206 of solid-state light source 202 and the size of light guide 204 may be chosen so that the etendue of solid-state light source 202 closely approximates, or matches, the etendue of light guide 204. Due to the concave shape of concave light emitting surface 206, more light rays 210 may enter light guide 204 and stay in light guide 204 via total internal reflection than in the case of the flat light emitting surface 106 seen in FIG. 1. Thus, the angle of incidence 208, labeled "θ" in FIG. 2, may be within the numerical aperture (NA) of light guide 204 for most of the light rays 210 emitted by solid-state light source 202. By using a concave light emitting surface 206 the etendue of solid-state light source 202 may more closely match the etendue of light guide 204 so that more light rays 210 are within the numerical aperture of light guide 204, increasing the efficiency of the optical coupling. By increasing the optical coupling efficiency, the smallest feasible size may be used for light guide 204 so that the diameter, or size, of light guide 204 closely approximates the diameter, or size, of solid-state light source 202.

Fiber fed illumination system 200 may also include coupling assembly 212. Coupling assembly 212 may include plastic dome 214. Plastic dome 214 may be drilled to form a hole 216 of proper dimensions to accept light guide 204. Coupling assembly 212 may include a cavity 218, surrounding concave light emitting surface 206 of solid-state light source 202. Cavity 218 may be filled with optical gel 220, which may be an index matching gel for the purpose of bridging the gap, or transmitting light, between the light source and the light guide when the light guide is not bonded to the light emitting surface. Fiber fed illumination system 200 may also include lead wires 222 for providing electrical connection to a source of power for solid-state light source 202.

It should be understood, of course, that the foregoing relates to preferred embodiments of the invention and that modifications may be made without departing from the spirit and scope of the invention as set forth in the following claims.

What is claimed is:

1. A fiber fed illumination system comprising:
   a solid-state light source having a light emitting surface;
   a light guide, wherein said solid-state light source is bonded to said light guide; and
   a coupling assembly including a plastic dome with a hole, said hole being dimensioned to accept said light guide, wherein said plastic dome forms a cavity surrounding said light emitting surface, said cavity filled with an index matching optical gel, wherein said light guide is placed next to the light emitting surface of said solid-state light source, whereby light from said solid-state light source is transmitted within said light guide, wherein said solid state light source has a concave light emitting surface and the light guide is positioned relative to the concave light emitting surface such that light emitted from said concave light emitting surface is counted efficiently into the light guide, and wherein an etendue of said solid-state light source matches an etendue of said light guide.

2. The fiber fed illumination system of claim 1, wherein said solid state light source comprises an LED.

3. The fiber fed illumination system of claim 1, wherein said light guide comprises an optical fiber.

4. The fiber fed illumination system of claim 1, wherein said light guide comprises a fiber bundle.

5. A fiber fed illumination system comprising:
   a solid-state light source having a light emitting surface;
   a light guide; and
   a coupling assembly wherein said light guide is placed next to the light emitting surface of said solid-state light source and said light guide is bonded to said light source, said coupling assembly further comprising a plastic dome with a hole, said hole being dimensioned to accept said light guide, and said plastic dome forming a cavity surrounding said light emitting surface, said cavity filled with an index matching optical gel, whereby light from said solid-state light source is transmitted within said light guide, wherein said solid state light source has a concave light emitting surface and the light guide is positioned relative to the concave light emitting surface such that light emitted from said concave light emitting surface is coupled efficiently into the light guide.

6. The fiber fed illumination system of claim 5, wherein said solid state light source comprises an LED.

7. The fiber fed illumination system of claim 5, wherein an etendue of said solid-state light source matches an etendue of said light guide.

8. The fiber fed illumination system of claim 5, wherein said light guide comprises an optical fiber.

9. The fiber fed illumination system of claim 5, wherein said light guide comprises a fiber bundle.

10. The fiber fed illumination system of claim 5, wherein the light guide is positioned relative to the concave light emitting surface such that light emitted from said concave light emitting surface remains within the light guide by total internal reflection.

11. A coupling assembly for optically coupling a light guide to a solid-state light source having a light emitting surface, comprising a plastic dome with a hole, said hole being dimensioned to accept said light guide, and said plastic dome forming a cavity surrounding said light emitting surface, said cavity filled with an optical gel, wherein said light guide is in contact with said light emitting surface, and whereby light from said solid-state light source is transmitted within said light guide, wherein said solid state light source has a concave light emitting surface and the dome is configured for positioning the light guide relative to the concave light emitting surface such that light emitted from said concave light emitting surface is coupled efficiently into the light guide.

12. The coupling assembly of claim 11, wherein said light guide is bonded to said solid-state light source.

13. The coupling assembly of claim 11, wherein an etendue of said solid-state light source matches an etendue of said light guide.

14. The coupling assembly of claim 11, wherein a size of said light guide closely approximates a size of said solid-state light source.

15. The coupling assembly of claim 11, wherein said solid state light source comprises an LED.

16. The coupling assembly of claim 11, wherein said light guide comprises an optical fiber.

17. The coupling assembly of claim 11, wherein said light guide comprises a fiber bundle.

18. A fiber fed illumination system comprising:

a solid-state light source comprising an LED having a light emitting surface;

a light guide comprising a fiber optic; and a coupling assembly wherein said light guide is placed next to the light emitting surface of said solid-state light source and said light guide is bonded to said solid-state light source, said coupling assembly further comprising a plastic dome with a hole, said hole being dimensioned to accept said light guide, and said plastic dome forming a cavity surrounding said light emitting surface, said cavity filled with an index matching optical gel, wherein a size of said solid-state light source substantially matches a size of said light guide, and the light guide is positioned relative to the light emitting surface such that light emitted from said light emitting surface is counted efficiently into the light guide, whereby light from said solid-state light source is transmitted within said light guide;

wherein said solid-state light source has a concave light emitting surface and the light guide is positioned relative to the concave light emitting surface such that light emitted from said concave light emitting surface is coupled efficiently into the light guide;

wherein the light guide is positioned relative to the concave light emitting surface such that light emitted from said concave light emitting surface remains within the light guide by total internal reflection; and wherein an etendue of said solid-state light source matches an etendue of said light guide.

19. The fiber fed illumination system of claim 18, wherein a size of said light guide closely approximates a size of said solid-state light source.

20. A method of optically coupling a light guide to a solid-state light source comprising steps of:

providing the solid-state light source wherein said solid-state light source has a light emitting surface;

matching a size of said light guide to a size of said solid-state light source, whereby a light guide of size closely approximating said size of said solid-state light source is used;

placing said light guide next to said light emitting surface;

transmitting light from said solid-state light source into said light guide such that light emitted from said light emitting surface is coupled efficiently into the light guide;

matching an etendue of said light guide to an etendue of said solid-state light source;

bonding said light guide to said light source;

surrounding said light emitting surface with a cavity formed by a plastic dome and filling said cavity with an index matching optical gel.

21. The method of claim 20, wherein said providing step comprises providing a solid-state light source having a concave light emitting surface and the light guide is positioned relative to the concave light emitting surface such that light emitted from said concave light emitting surface is coupled efficiently into the light guide.

22. The method of claim 20, wherein said solid-state light source comprises an LED and said light guide comprises a fiber optic.

* * * * *